United States Patent

Hübner et al.

[11] Patent Number: 6,063,968
[45] Date of Patent: May 16, 2000

[54] METHOD FOR THE PRODUCTION OF TRIMETHYLHYDROQUINONE

[75] Inventors: Frank Hübner, Ober-Ramstadt; Steffen Krill, Speyer; Bernd Drapal, Alzenau; Hermann Schmitt, Rodenbach; Klaus Huthmacher, Gelnhausen; Herbert Tanner, Hanau, all of Germany

[73] Assignee: Degussa Aktiengesellschaft, Frankfurt, Germany

[21] Appl. No.: 08/855,270

[22] Filed: May 14, 1997

[30] Foreign Application Priority Data

May 14, 1996 [DE] Germany ........................ 196 19 387
Jul. 11, 1996 [DE] Germany ........................ 196 27 977

[51] Int. Cl.[7] .................................................. C07C 37/00
[52] U.S. Cl. ............................................................ 568/772
[58] Field of Search ............................................... 568/772

[56] References Cited

U.S. PATENT DOCUMENTS

T900,015 7/1972 Thweatt et al. ..................... 260/621

FOREIGN PATENT DOCUMENTS 2149159 4/1972 Germany.

OTHER PUBLICATIONS

Howells et al., "Trifluoromethanesulfonic acid and derivatives", Chemical Reviews, vol. 77, pp. 69–92, 1977.

Y.A. Joe et al., Characteristic Oxidative Aromatization Pattern of Isophorone, 4–Hydroxyisophorone, and Rearrangement of 4–Oxoisophorone Under a Strong Acidic Condition, Bulletin of the Korean Chemical Society, Jun. 1991, 253–254.

*Primary Examiner*—Jose' G. Dees
*Assistant Examiner*—Barbara Badio
*Attorney, Agent, or Firm*—Pillsbury Madison & Sutro LLP

[57] ABSTRACT

The invention relates to an improved method for the production of 2,3,5-trimethylhydroquinone by rearranging 4-oxo-isophorone (keto-isophorone, 3,5,5-trimethylcyclohex-2-en[e]-1,4-dione) to a trimethylhydroquinone diester and by its subsequent saponification.

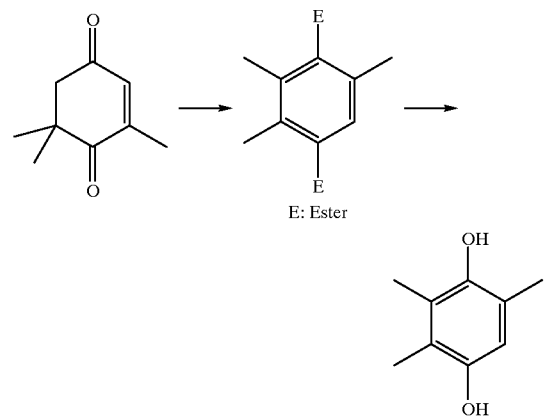

2 Claims, No Drawings

METHOD FOR THE PRODUCTION OF TRIMETHYLHYDROQUINONE

This application is based on Application Nos. 19619387.7 and 19627977.1 filed in Germany on May 14, 1996 and Jul. 11, 1996, respectively, the content of which is incorporated herein by reference.

BACKGROUND OF THE INVENTION

1. Field of the Invention

The invention relates to an improved method for the production of 2,3,5-trimethylhydroquinone by rearranging 4-oxo-isophorone (keto-isophorone, 3,5,5-trimethylcyclohex-2-en[e]-1,4-dione) to a trimethylhydroquinone diester and by its subsequent saponification.

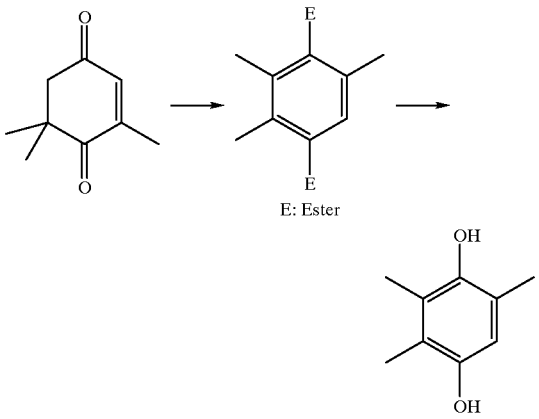

E: Ester

Trimethylhydroquinone is an important initial product for producing vitamin E.

2. The Prior Art

The rearrangement of keto-isophorone in the gaseous phase with a zeolite into trimethylhydroquinone is already known (DE 26 46 172 C2). However, the yields in this reaction are only small (50% at 30% conversion) and thus unsatisfactory for an economical method. In another method (Y. A. Joe, Y. M. Goo, Y. Y. Lee, *Bull. Korean Chem. Soc.* 1991, 12, 253) the rearrangement is carried out in 5% solution in acetic anhydride by the addition of five equivalents of concentrated sulfuric acid. Trimethylhydroquinone esters are obtained thereby with only 31% yield, so that even this method is not economical.

According to a third method (DE-OS 2 149 159) keto-isophorone can be reacted in the presence of a protonic acid in acetic anhydride to trimethylhydroquinone diacetate, which is subsequently saponified to 2,3,5-trimethylhydroquinone. Disadvantages in this method are the use Of large amounts of acetic anhydride (5–10 mole/mole ketoisophorone), Of large amounts of the catalytic acid (up to 150 molar %)

As well as the rather moderate yield with a maximum of 66%.

SUMMARY OF THE INVENTION

A method now has been found for the production of trimethylhydroquinone (TMHQ) by reacting keto-isophorone with an acylating agent in the presence of catalytic amounts of a protonic acid and by subsequent saponification of the trimethylhydroquinone ester formed at first which is characterized in that trifluoromethane sulfonic acid, chlorosulfonic acid, polyphosphoric acid or oleum or mixtures of these acids in an amount of 0.1 to 50% by weight, especially 0.5 to 25% by weight relative to the final ion, are used as protonic acid. It is preferable to use >2 to 4 moles, especially 2.1 to 3 moles of one of the generally known acylating agents per mole keto-isophorone.

The acylating agent used in accordance with the invention is preferably a carboxylic acid anhydride or an enol ester. In particular, a carboxylic acid anhydride of the general formula

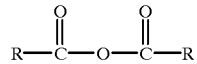

is used in which R is an optionally substituted, aliphatic, alicyclic or aromatic group with 1 to 8 carbon atoms which group can optionally contain 1 to 3 halogen atoms. An acid anhydride used with particular preference is acetic anhydride. Other suitable acid anhydrides are anhydrides of propionic acid, butyric acid, isobutyric acid, cyclohexane carboxylic acid, benizoic acid, chloroacetic acid, trifluoroacetic acid and trifluoromethane sulfonic acid.

In a preferred embodiment the TMHQ diacetate produced is saponified without isolation, optionally after the distilling off of non-reacted acetic anhydride by the addition of water of dilute acid, especially sulfuric acid, and heating the mixture to a boil. The TMHQ produced is then filtered off.

However, the TMHQ diacetate produced can also be separated after the addition of water from the reaction mixture, hydrolyzed in dilute acid, especially sulfuric acid, in the presence of a phase agent and the TMHQ produced separated, especially by filtering.

All organic solvents with a certain miscibility with water can be used as phase agent in the saponification of even the isolated trimethylhydroquinone diester. It is especially advantageous to use acetic acid, n-butanol and n-butylacetate or mixtures of the cited solvents.

In order to produce 2,3,5-trimethylhydroquinone in accordance with the method of the invention, 0.2 mole keto-isophorone, for example, is added dropwise in a one-pot method to a mixture of >0.4–0.6 mole acetic anhydride and 0.1–50% by weight, especially 0.5–25% by weight, relative to keto-isophorone, of one of the cited, very strong acids within 1 to 3 h at 0–60° C. and then heated 1 to 7 h to approximately 25–70° C. Then remnants of the acetic anhydride are hydrolyzed by the addition of a sufficient amount of water. If necessary, sulfuric acid, preferably approximately 30%, is added to the suspension produced and the mixture heated 1 to 5 h to a boil. Then a part of the solvent is distilled off and replaced by the same amount of water, the suspension cooled down to room temperature and the precipitated trimethylhydroquinone separated off.

The precipitated trimethylhydroquinone diester can be separated off in the same way after the first addition of water and separately saponified. For this, the trimethylhydroquinone diester is suspended, e.g., in a sufficient amount of a dilute acid, preferably 30% sulfuric acid, and a phase agent such as, e.g., n-butanol and then heated 1 to 7 h to a boil. Thereafter, distillate is removed and then the same amount of water added to the bottom. The trimethylhydroquinone which is then precipitated is separated off and purified by post-washing.

The invention is explained further in the following using exemplary embodiments.

Significant advantages over the state of the art result in the production of 2,3,5-trimethylhydroquinone in accordance with the invention:

The yields according to the method of the invention are up to 25% greater than in the cited literature and are between 85 and 90%.

The amounts of catalyst required are approximately 0.1 to 50% compared to 150% in the literature.

Only >2 to 4 moles of a carboxylic acid anhydride per mole keto-isophorone are required compared to 5 to 10 moles in the literature.

The saponification of the isolated trimethylhydroquinone ester with aqueous acid succeeds preferably in a simple manner in the presence of a phase agent.

DETAILED DESCRIPTIONS OF PREFERRED EMBODIMENTS OF THE INVENTION

EXAMPLE 1

30.5 g (0.2 mole) keto-isophorone (98%) was added dropwise at 30° C.–40° C. to a solution of 61 g (0.6 mole) acetic anhydride and 0.34 g (2.3 mmoles) trifluoromethane sulfonic acid within 1.5 h. The mixture was then allowed to react 3 h at 40° C. After the end of the reaction the mixture was compounded with 125 ml water under cooling, the precipitated trimethylhydroquinone diacetate removed by suction, post-washed and dried 14 h at 55° C. in a vacuum.

Yield: 45.0 g (95% of theory) GC: 94.5% TMHQ diacetate

EXAMPLE 2

43 g (0.18 mole) TMHQ diacetate were dissolved under heating in a mixture of 100 ml 30% sulfuric acid and 15 ml n-butanol and then heated 4 h to a boil. Then 80 ml distillate were removed within 45 min and compounded with 100 ml water. The precipitated trimethylhydroquinone was removed by suction at 20° C., post-washed and dried 14 h at 55° C. in a vacuum.

Yield: 26.2 g (95% of theory) HPLC: 98.5%

EXAMPLE 2a

In a further saponification, instead of n-butanol and the 30% sulfuric acid a mixture of 50 ml of the distillate from test 2, 30 g sulfuric acid and 50 ml water was used.

EXAMPLE 3

The test of example 1 was repeated. This time 30 g of a mixture of acetic anhydride and acetic acid were distilled off after the reaction. The remaining workup took place analogously.

Yield: 45.5 g TMHQ diacetate (96% of theory)

EXAMPLE 4

The test of example 2 was repeated. This time the mixture was cooled down to −10° C. before the filtration of the product.

Yield: 26.9 g TMHQ (97% of theory) HPLC: 95%

EXAMPLES 5–7

The test of example 1 was repeated, but instead of trifluoromethane sulfonic acid other catalysts were used this time.

| Consec. No. | Catalyst | Amount cat. In (% by weight) | Reaction time Temperature (h/° C.) | Yield TMHQ-DA (%) |
|---|---|---|---|---|
| 5 | Chlorosulfonic acid | 7 | 3   75 | 93 |
| 6 | Oleum 65% SO$_3$ | 10 | 3   35 | 94 |
| 7 | Oleum 30% SO$_3$ | 8 | 7   35 | 94 |

EXAMPLE 8 (direct variant)

30.5 g (0.2 mole) keto-isophorone were added dropwise within 1.5 h at 10–25° C. to a mixture of 61 g (0.6 mole) acetic anhydride and 3 g oleum (65% SO$_3$) and the mixture then heated 4 h to 40° C. The mixture was then hydrolyzed by the addition of 90 ml water. 47 g sulfuric acid were added to the suspension produced and the mixture heated 3 h to a boil. The further workup took place analogously to example 2.

Yield: 27 g TMHQ (89% of theory) HPLC: 98.5%

What is claimed is:

1. A method of producing trimethylhydroquinone (TMHQ) by reacting ketoisopherone with an acylating agent in the presence of catalytic amounts of protonic acid to form a trimethylhydroquinone ester, and subsequently saponifying the trimethylhydroquinone ester, wherein the acid is trifluoromethane sulfonic acid, chlorosulfonic acid, polyphosphoric acid or oleum or mixtures of these acids, and wherein TMHQ diacetate produced is separated from the reaction mixture after the addition of water and saponified using dilute acid in the presence of a phase agent, and TMHQ produced thereby is separated off.

2. The method according to claim 1, wherein acetic acid, n-butanol or n-butylacetate or their mixtures is used as a phase agent.

* * * * *